(12) United States Patent
Purdy et al.

(10) Patent No.: US 7,682,530 B2
(45) Date of Patent: Mar. 23, 2010

(54) CRYSTALLINE COLLOIDAL ARRAYS RESPONSIVE TO AN ACTIVATOR

(76) Inventors: Sean Purdy, 108 Pamela Dr., Allison Park, PA (US) 15101; Noel Vanier, 405 Potomac Ct., Wexford, PA (US) 15090; Xiangling Xu, 106 Woodshire Rd., Pittsburgh, PA (US) 15215; Robert Cavlovich, 117 Chowning Ct., Gibsonia, PA (US) 15044

( * ) Notice: Subject to any disclaimer, the term of this patent is extended or adjusted under 35 U.S.C. 154(b) by 487 days.

(21) Appl. No.: 11/672,226

(22) Filed: Feb. 7, 2007

(65) Prior Publication Data

US 2008/0185498 A1 Aug. 7, 2008

(51) Int. Cl.
*G02B 5/23* (2006.01)
(52) U.S. Cl. ...................................... 252/586; 427/162
(58) Field of Classification Search ............. 250/201.1; 382/100; 427/162; 252/586
See application file for complete search history.

(56) References Cited

U.S. PATENT DOCUMENTS

| | | | |
|---|---|---|---|
| 4,833,172 A | 5/1989 | Schwarz et al. | |
| 5,281,370 A | 1/1994 | Asher et al. | |
| 5,854,078 A | 12/1998 | Asher et al. | |
| 6,114,023 A | 9/2000 | Schwarz et al. | |
| 6,187,599 B1 | 2/2001 | Asher et al. | |
| 6,753,191 B2 | 6/2004 | Asher et al. | |
| 6,894,086 B2 | 5/2005 | Munro et al. | |
| 7,008,567 B2 | 3/2006 | Foulger et al. | |
| 2004/0191496 A1 | 9/2004 | Rearick et al. | |
| 2006/0141228 A1 | 6/2006 | Rearick et al. | |
| 2007/0165903 A1* | 7/2007 | Munro et al. | 382/100 |

FOREIGN PATENT DOCUMENTS

| | | |
|---|---|---|
| WO | 03/054259 | 7/2003 |
| WO | 2006/069702 | 7/2006 |

OTHER PUBLICATIONS

Fudouzi, Hiroshi et al., "Colloidal Crystals with Tunable Colors and Their Use as Photonic Papers", Langmuir, 2003, pp. 9653-9660, vol. 19, American Chemical Society, USA.
Jethmalani, Jagdish M. et al., "Diffraction of Visible Light by Ordered Monodisperse Silica-Poly(methyl acrylate) Composite Films", Chem. Mater., 1996, pp. 2138-2146, vol. 8, American Chemical Society, USA.
Zeng, Fang et al., "Preparation and dynamic viscoelastic properties of strengthened solidified colloidal crystals", Reactive & Functional Polymers, 2002, pp. 39-44, vol. 53, Elsevier Science B.V.
Endo, Tatsuro et al., "Colorimetric detection of volatile organic compounds using a colloidal crystal-based chemical sensor for environmental applications", Sensors and Actuators B, 2007, pp. 589-595, vol. 125, Elsevier B.V.

* cited by examiner

*Primary Examiner*—Seung C Sohn
(74) *Attorney, Agent, or Firm*—Diane R. Meyers

(57) ABSTRACT

A method of producing a radiation diffractive sensor that diffracts radiation according to Bragg's law is disclosed. The sensor is produced by forming an ordered periodic array of particles on a substrate, coating the array of particles with a polymeric matrix, curing the matrix to fix the array of particles within the matrix and contacting the fixed array with an activator, wherein the activator shifts the wavelength of radiation diffracted by the sensor from a first wavelength to a second wavelength.

30 Claims, No Drawings

CRYSTALLINE COLLOIDAL ARRAYS RESPONSIVE TO AN ACTIVATOR

FIELD OF THE INVENTION

This invention relates to sensors produced from radiation diffractive materials, more particularly to radiation diffractive sensors which, when contacted with an activator composition, exhibit a change in the wavelength of the diffraction.

BACKGROUND OF THE INVENTION

Radiation diffractive materials based on crystalline colloidal arrays have been used for a variety of purposes. A crystalline colloidal array (CCA) is a three-dimensional ordered array of mono-dispersed colloidal particles. The particles are typically composed of a polymer latex such as polystyrene or an inorganic material, such as silica.

Such colloidal dispersions of particles can form crystalline structures having lattice spacings that are comparable to the wavelength of ultraviolet, visible or infrared radiation. These crystalline structures have been used for filtering narrow bands of selected wavelengths from a broad spectrum of incident radiation, while permitting the transmission of adjacent wavelengths of radiation. Prior devices have been created by dispersing particles in a liquid medium, whereby the particles self-align into an ordered array. The particles are fused together by mutual polymerization or by introducing a solvent that swells and fuses the particles together.

In other uses of CCAs, an ordered array is fixed in a matrix and may be used as colorants when the fixed array diffracts radiation in the visible spectrum. Alternatively, CCAs are fabricated to diffract radiation for use as optical filters, optical switches and optical limiters. While these CCAs use constant interparticle spacing, a CCA may function as a sensor when the interparticle spacing varies in response to stimuli.

Recently, such sensors have been produced from hydrogels containing a CCA polymerized within the hydrogel. The polymers of the hydrogel surrounding the CCA change conformation in response to a specific external stimulus. For example, the volume of the hydrogel can change in response to stimuli, including the presence of chemicals, such as metal ions in solution and organic molecules, such as glucose, making the devices useful for chemical analysis. In hydrogel-based devices, mono-dispersed highly charged colloidal particles are dispersed in a low-ionic strength liquid media. The particles self-assemble into a CCA due to their electrostatic charges. These ordered structures diffract radiation according to Bragg's law, wherein the radiation meeting the Bragg conditions are reflected while adjacent spectral regions that do not meet the Bragg conditions are transmitted through the device.

An ordered periodic array of particles that diffracts radiation according to Bragg's law satisfies the equation:

$$m\lambda = 2nd \sin\theta$$

where m is an integer, $\lambda$ is the wavelength of reflected radiation, and n is the effective refractive index of the array, d is the distance between the layers of particles, and $\theta$ is the angle that the reflected radiation makes with the plane of a layer of particles. Incident radiation is partly reflected at an uppermost layer of particles in the array at angle $\theta$ to the plane of the first layer and is partially transmitted to underlying layers of the particles. While some absorption incident radiation occurs as well, a portion of the transmitted radiation is partially reflected at the second layer of particles in the array at angle $\theta$ and partially transmitted to the underlying layers of particles. This feature of partial reflection at angle $\theta$ and partial transmission to the underlying layers of particles continues through the thickness of the array. The wavelength ($\lambda$) of diffracted radiation can be controlled by the dimension d, which may be the distance between the planes of the centers of the particles in each layer. Initially, the diffracted wavelength $\lambda$ is proportional to the particle diameter for an array of packed particles. However, when distance (d) between layers of particles in a periodic ordered array increases, the wavelength of diffracted radiation also increases. Sensor devices that increase the interspatial volume within the device in response to a specific chemical species increase the interspatial distance between layers of particles, thereby altering the wavelength of diffracted radiation.

In a hydrogel-based CCA, when the volume of the hydrogel changes, the diffraction wavelength of the CCA changes. Such CCA devices that are based on hydrogels typically contain a large percentage of water, such as about 30% by volume. These hydrogel-based CCAs are fragile and have a propensity for significant changes in their optical performance when the water content of the CCA changes.

To overcome these drawbacks of hydrogel-based CCAs, one approach has been to prepare a hydrogel-based CCA, dehydrate the hydrogel matrix surrounding the CCA and then back fill the array with a polymerizable monomer. The monomer is polymerized to produce an essentially water-free polymerized crystalline colloidal array. These arrays respond to certain environmental stimuli, such as compressive stress (thereby altering the lattice spacing) to alter the diffracted wavelength of the CCA.

However, these prior systems of hydrogel-based CCAs have significant production and handling drawbacks. A need exists for a more robust CCA, which exhibits radiation diffracting properties in response to applied chemical stimuli and the like and which substantially returns to its initial optical characteristics upon removal of the stimulus.

SUMMARY OF THE INVENTION

The present invention is directed to a radiation diffraction sensor comprising an ordered periodic array of particles formed on a substrate and a solid matrix composition coated onto the array of particles, wherein the matrix composition is selected to be responsive to an activator, such that exposure to the activator shifts the wavelength of radiation diffracted by the sensor from a first wavelength to a second wavelength. The invention also includes a method of producing a sensor comprising forming an ordered periodic array of particles on a substrate; coating the array of particles with a matrix; and curing the matrix to fix the particles within the matrix, wherein the matrix is selected to be responsive to an activator, such that exposure to the activator shifts the wavelength of radiation diffracted by the sensor.

The invention also includes a method of authenticating an article comprising forming an ordered periodic array of particles on a substrate; coating the array of particles with a matrix; curing the matrix to fix the array of particles within the matrix to produce a sensor that diffracts radiation at a first wavelength; applying the sensor to an article; and contacting the sensor with an activator, such that the activator shifts the wavelength of diffraction, wherein the shifted wavelength of diffraction indicates the authenticity of the article.

DETAILED DESCRIPTION OF THE INVENTION

The present invention includes radiation diffractive sensors, where the sensors diffract radiation in the visible and/or non-visible spectrum, and methods for making the same. The radiation diffractive sensors include an ordered periodic array of particles held in a polymeric matrix. The array includes a plurality of layers of particles and satisfies Bragg's law of:

$$m\lambda = 2nd \sin \theta$$

where m is an integer, n is the effective refractive index of the array and d is the distance between the layers of particles, and λ is the wavelength of radiation reflected from the plane a layer of the particles at angle θ. As used herein, "a" wavelength of diffracted radiation includes a band of the electromagnetic radiation spectrum. For example, reference to a wavelength of 600 nm may include 590 to 610 nm.

Various compositions may be used for the particles, including, but not limited to, organic polymers such as polystyrene, polyurethane, acrylic polymers, alkyd polymers, polyesters, siloxane-containing polymers, polysulfides, epoxy-containing polymers and inorganic materials such as metal oxides (e.g., alumina, silica, zinc oxide, or titanium dioxide) or semiconductors such as cadmium. Alternatively, the particles may have a core-shell structure where the core can be produced from the same materials as the above-described unitary particles. The shell may be produced from the same polymers as the core material, with the polymer of the particle shell differing from the core material for a particular array of the core-shell particles. The core material and the shell material can have different indices of refraction. In addition, the refractive index of the shell may vary as a function of the shell thickness in the form of a gradient of refractive index through the shell thickness. The shell material is non-film-forming, whereby the shell material remains in position surrounding each particle core without forming a film of the shell material so that the core-shell particles remain as discrete particles within the polymeric matrix.

Typically, the particles are generally spherical. For coreshell particles, the diameter of the core may constitute 70 to 95% of the total particle diameter or 90% of the total particle diameter with the shell constituting the balance of the particle diameter and having a radial thickness dimension.

In one embodiment, the particles with a unitary structure (not core-shell) are produced via emulsion polymerization in the presence of a surfactant, yielding a dispersion of charged particles. Suitable surfactants for dispersion of latex particles include, but are not limited to, sodium styrene sulfonate, sodium 1-allyloxy-2-hydroxypropyl sulfonate (commercially available as SIPOMER COPS-I from Rhodia Corporation), acrylamide propyl sulfonate, and sodium allyl sulfonate. Particularly useful surfactants are those that are minimally soluble in the dispersing fluid (e.g., water) of the particle dispersion. The charged particles are purified from the dispersion by techniques such as ultra-filtration, dialysis or ion-exchange to remove undesired materials, such as unreacted monomer, small polymers, water, initiator, surfactant, unbound salt and grit (agglomerated particles) to produce a monodispersion of charged particles. Ultra-filtration is particularly suitable for purifying charged particles. When the particles are in a dispersion with other materials, such as salts or by-products, the repelling forces of the charged particles can be mitigated; therefore, the particle dispersion is purified to essentially contain only the charged particles, which then readily repel each other and form an ordered array.

Upon removal of the excess raw material, by-products, solvent and the like, electrostatic repulsion of the charged particles causes the particles to align themselves into an ordered array. The purified dispersion of particles is applied to a substrate and dried. The dispersion of particles applied to the substrate may contain 10-70 vol. % of charged particles or 30-65 vol. % of charged particles. The dispersion can be applied to the substrate by dipping, spraying, brushing, roll-coating, curtain coating, flow-coating or die-coating to a desired thickness. The wet coating may have a thickness of 4-50 microns, such as 40 microns. Upon drying, the material contains essentially only the particles that have self-aligned in a Bragg array and diffract radiation accordingly.

The substrate may be a flexible material, such as metal sheet or foil (e.g. aluminum foil), paper or a film (or sheet) of polyester or polyethylene terephthalate (PET), or an inflexible material, such as glass or plastic. By "flexible" it is meant that the substrate can undergo mechanical stresses, such as bending, stretching, compression and the like, without significant irreversible change. One suitable substrate is a microporous sheet. Some examples of microporous sheets are disclosed in U.S. Pat. Nos. 4,833,172; 4,861,644 and 6,114,023, which are incorporated herein by reference. Commercially available microporous sheets are sold under the designation TESLIN by PPG Industries, Inc. Other suitable flexible substrates include natural leather, synthetic leather, finished natural leather, finished synthetic leather, suede, vinyl nylon, ethylene vinyl acetate foam (EVA foam), thermoplastic urethane (TPU), fluid-filled bladders, polyolefins and polyolefin blends, polyvinyl acetate and copolymers, polyvinyl chloride and copolymers, urethane elastomers, synthetic textiles and natural textiles.

In certain embodiments, the flexible substrates are compressible substrates. "Compressible substrate" and like terms refer to substrates capable of undergoing a compressive deformation and returning to substantially the same shape once the compressive deformation has ceased. The term "compressive deformation" means a mechanical stress that reduces the volume at least temporarily of a substrate in at least one direction.

"EVA foam" can comprise open cell foam and/or closed cell foam. "Open cell foam" means that the foam comprises a plurality of interconnected air chambers; "closed cell foam" means that the foam comprises discrete closed pores. EVA foam can include flat sheets or slabs or molded EVA foams, such as shoe midsoles. Different types of EVA foam can have different types of surface porosity. Molded EVA can comprise a dense surface or "skin", whereas flat sheets or slabs can exhibit a porous surface. Polyurethane substrates according to the present invention include aromatic, aliphatic and hybrid (hybrid examples are silicone polyether or polyester urethane and silicone carbonate urethane) polyester or polyether based thermoplastic urethane. By "plastic" is meant any of the common thermoplastic or thermosetting synthetic materials, including thermoplastic olefins ("TPO") such as polyethylene and polypropylene and blends thereof, thermoplastic urethane, polycarbonate, sheet molding compound, reaction-injection molding compound, acrylonitrile-based materials, nylon, and the like. A particular plastic is TPO that comprises polypropylene and EPDM (ethylene propylene diene monomer).

In another embodiment of the invention, core-shell particles are produced by dispersing core monomers with initiators in solution to produce core particles. Shell monomers are added to the core particle dispersion, along with an emulsifier and/or surfactant (as described above for unitary particles), such that the shell monomers polymerize onto the core particles. A dispersion of the core-shell particles is purified as described above to produce a dispersion of only the charged core-shell particles, which then form an ordered array on a substrate when applied thereto.

The dried array of particles (unitary or core-shell) on a substrate is fixed in a polymeric matrix by coating the array of particles with a fluid curable matrix composition that includes monomers or other polymer precursor materials, followed by curing of the matrix composition. As disclosed in U.S. Pat. No. 6,894,086 (incorporated herein by reference), the particles that have self-aligned in the dried array can be interpenetrated with the fluid curable matrix composition, such as an ultraviolet (UV) curable composition. The curable matrix composition material may be coated onto the dried array of particles via dipping, spraying, brushing, roll coating, gravure coating, curtain coating, flow coating, slot-die coating, or ink-jet coating. By coating, it is meant that the polymer precursor material covers the entirety of the array and fills at least some of the interstitial spaces between the particles. The matrix composition is cured (such as by exposure to UV radiation) to fix the array of packed particles. Other curing mechanisms may be used to fix the matrix composition around the particles.

For a radiation diffractive sensor having the core-shell particles, upon interpenetration of the array with the fluid curable matrix composition, some of the monomers of the matrix may diffuse into the shells, thereby increasing the shell thickness (and particle diameter) until the matrix composition is cured. Solvent may also diffuse into the shells and create swelling. The solvent is ultimately removed from the array, but this swelling from solvent may impact the final dimensions of the shell. The length of time between interpenetration of monomers into the array and curing of the monomers, in part, determines the degree of swelling by the shells.

The radiation diffractive sensor of the present invention is non-gelatinous and substantially solid. By non-gelatinous, it is meant that the radiation diffractive sensor does not contain a fluidizing material, such as water, and is not a hydrogel. Nor is the product sensor produced from a hydrogel, which will be understood by those skilled in the art as resulting in a different product than that presently claimed. In certain embodiments, the radiation diffractive sensor of the present invention substantially only includes the particles and the polymeric matrix with some possible residual solvent and, thus, is substantially solid. The volumetric ratio of the particles to the polymer matrix in the radiation diffractive sensor is typically about 25:75 to about 80:20.

The radiation diffractive sensor may be applied to an article in various ways. The radiation diffractive sensor may be produced on a substrate and then removed from the substrate and comminuted into particulate form, such as in the form of flakes. The comminuted radiation diffractive sensor may be incorporated as an additive in a coating composition, such as paint or ink for applying to an article. Alternatively, the radiation diffractive sensor may be applied directly to an article, whereby the substrate is a surface of an article, such as the packaging and/or the housing of an article of manufacture. By way of example, articles of manufacture may include consumer goods (including pharmaceutical products or food items) with the substrate being the packaging for the goods. Alternatively, the article itself may serve as a substrate by applying the array of particles directly to the housing of the article such as the housing of electronic devices or directly to goods such as clothing, footwear, sports equipment and the like. Similarly, the article may be an identification document, legal document or other document requiring confirmation of its authenticity.

In addition, the radiation diffractive sensor may be produced in the form of a film or sheet, which is then applied to an article such as via an adhesive or the like. It should be appreciated that these methods of producing a sensor on a substrate differ from other techniques for producing sensors that do not first form an ordered array directly on a substrate followed by coating the array with a matrix material.

The radiation diffractive sensor is responsive to the presence of one or more activators that cause the matrix to diffract at a different wavelength. According to the present invention, the matrix composition is selected so that contact of the matrix with a particular activator alters the dimensions of the matrix, and/or changes the refractive index of the matrix. If the dimensions are changed, the interspatial distances between particles and/or layers of particles in the array may be changed. An "activator" as used herein is any material that causes the dimensions of and/or the refractive index of the matrix to change. "Change the dimensions of the matrix" and like terms means that the matrix expands (i.e. "swells") or contracts (i.e. "shrinks") in response to the activator. "Change the refractive index of the matrix" means that the effective refractive index of the matrix changes in response to the activator, hence changing the wavelength and/or intensity of radiation diffracted by the sensor. It is possible to change the refractive index of the matrix without changing its dimensions and vice versa. The activator can be, for example, a chemical species, such as water or organic solvents, or a liquid containing a solute or a gas. The matrix is chosen to be responsive to a particular activator. "Responsive to" an activator means that the activator changes the dimensions of the matrix and/or changes the refractive index of the matrix. In certain embodiments, when an activator contacts the matrix of the sensor, the activator becomes associated with the matrix and increases the matrix volume. This increase in matrix volume causes the layers of the particles to spread apart. According to Bragg's law, an increase in the interparticle distance (d), changes the wavelength ($\lambda$) of diffracted radiation from an initial or first wavelength ($\lambda_1$) to a second wavelength ($\lambda_2$) that may be longer than the initial wavelength. Alternatively, in other embodiments the second wavelength ($\lambda_2$) can be shorter that the initial wavelength ($\lambda_1$). The wavelengths $\lambda_1$ and $\lambda_2$ can be tuned by selecting the particle composition, particle size, matrix composition and/or activator composition. The particle and matrix compositions determine the effective refractive index (n) of the sensor. Particle size determines the initial distance (d) between layers of the array. The matrix composition and activator composition are selected so that the activator exhibits sufficient affinity with the matrix to remain within the matrix, causing the matrix to diffract a different wavelength. The wavelengths $\lambda_1$ and $\lambda_2$ may both be in the visible spectrum of radiation so that the presence of the activator is exhibited by a visible color shift. Both $\lambda_1$ and $\lambda_2$ may be in the invisible spectrum, wherein the wavelength shift is detectable with appropriate instrumentation. Alternatively, $\lambda_1$ may be in the invisible spectrum (UV or IR) while $\lambda_2$ is in the visible spectrum, wherein a color appears upon contact of the sensor with an activator. Likewise, $\lambda_1$ may be in the visible and $\lambda_2$ is in the invisible spectrum, such that a color of diffracted light disappears when the sensor contacts an activator. Any other wavelength combination is also within the scope of the present invention.

Upon removal of the activator (such as by evaporation), the matrix of the sensor may return at least substantially to the original diffraction wavelength, i.e. $\lambda_1$. By substantially, it is meant that the diffraction wavelength returns to within about 5-10 nm of its original wavelength. In theory, upon complete removal of the activator, the matrix will return to its original diffraction wavelength. However, in practice, some activator may remain within the matrix so that for certain matrix and activator pairs, the diffraction wavelength may not fully return to its original wavelength. In either case, upon complete return or substantial return of the sensor to its original state, the sensor functions to detect the presence or absence of the activator. The return of the matrix to at least substantially its original diffraction wavelength upon removal of the activator can be of any rate ranging from immediate to gradual. In certain embodiments, the sensor may be of a single use design in which the activator cannot be readily removed from the matrix to return the sensor to its original state.

In one embodiment, the matrix composition is a water soluble or hydrophilic acrylic polymer, with the activator being water. Suitable monomers for producing a water soluble or hydrophilic matrix include, but are not limited to, ethoxylated$_{15}$ trimethylolpropane triacrylate, ethoxylated$_{20}$ trimethylolpropane triacrylate, polyethylene glycol (600) diacrylate, polyethylene glycol (400) diacrylate, polyethylene glycol (200) diacrylate, and acrylic acid.

Other suitable monomers for producing a water soluble or hydrophilic polymer matrix may include polyethylene glycol (1000) diacrylate, methoxy polyethylene glycol (350) monoacrylate, methoxy polyethylene glycol (350) monomethacrylate, methoxy polyethylene glycol (550) monomethacrylate, methoxy polyethylene glycol (550) monoacrylate, ethoxylated$_{30}$ Bisphenol A diacrylate, 2(2-ethoxyethoxy) ethyl acrylate, acrylamide, hydroxyethyl acrylate, hydroxypropyl acrylate, polyethylene glycol (600) dimethacrylate, polyethylene glycol (400) dimethacrylate, ethoxylated$_{30}$ Bisphenol A dimethacrylate, hydroxyethyl methacrylate, and hydroxypropyl methacrylate.

Water soluble or hydrophilic polymers produced by these monomers are swellable with water. Application of water to a radiation diffractive sensor of the present invention having a matrix of a water soluble or hydrophilic polymer causes the matrix between the particles to receive water and swell. The water swelling increases the interspatial distances between the particles (the variable (d) of Bragg's law), thus increasing the wavelength of diffracted radiation.

Alternatively, the matrix may be a composition that is swelled by an organic solvent. Suitable organic solvent swellable matrix materials are polymers having an affinity for an organic solvent, meaning that the matrix polymer is swellable by an organic solvent to a degree by which a change in the wavelength of diffracted radiation is detectable. Suitable organic solvent swellable polymers may be produced from the following non-limiting monomers: alkoxylated hexanediol diacrylate, ethoxylated$_3$ trimethylolpropane triacrylate, pentaerythritol tetraacrylate, pentaerythritol triacrylate, propoxylated$_3$ trimethylolpropane triacrylate, propoxylated$_6$ trimethylolpropane triacrylate, 1,4-butanediol diacrylate, ethoxylated$_3$ Bisphenol A diacrylate, trimethylolpropane triacrylate, propoxylated$_2$ neopentyl glycol diacrylate, ethoxylated$_3$ trimethylolpropane triacrylate, ethoxylated$_6$ trimethylolpropane triacrylate, ethoxylated$_9$ trimethylolpropane triacrylate, ethoxylated$_3$ Bisphenol A dimethacrylate, neopentyl glycol diacrylate, and 1,6-hexanediol diacrylate.

Other suitable monomers for producing an organic solvent swellable acrylic polymer matrix may include propoxylated$_3$ glyceryl triacrylate, stearyl acrylate, tetrahydrofurfuryl acrylate, laurel acrylate, 2-phenoxyethyl acrylate, isodecyl acrylate, isoctyl acrylate, octyl acrylate, decyl acrylate, tridecyl acrylate, caprolactone acrylate, ethoxylated$_4$ nonylphenol acrylate, isobornyl acrylate, butyl acrylate, tetraethylene glycol diacrylate, triethylene glycol diacrylate, di-trimethylolpropane tetraacrylate, ethoxylated$_4$ pentaerythritol tetraacrylate, ethyl acrylate, 2-ethylhexyl acrylate, styrene, acrylonitrile, trimethylol propane triacrylate, methylmethacrylate, butyl methacrylate, cyclohexyl methacrylate, isobornyl methacrylate, lauryl methacrylate, polypropylene glycol monomethacrylate, propoxylated$_2$ allyl methacrylate, allyl methacrylate, ethoxy cetyl methacrylate, ethoxy stearyl methacrylate, ethoxylated$_2$ hydroxyethyl methacrylate, ethoxylated$_5$ hydroxyethyl methacrylate, ethoxylated$_{10}$ hydroxyethyl methacrylate, ethoxylated$_4$ nonyl phenol methacrylate, ethoxy triglycol methacrylate, tetrahydrofurfuryl methacrylate, isodecyl methacrylate, lauryl methacrylate, stearyl methacrylate, 2-phenoxyethyl methacrylate, glycidyl methacrylate, isobornyl methacrylate, tridecyl methacrylate, cyclohexane dimethanol dimethacrylate, ethoxylated$_4$ Bisphenol A dimethacrylate, ethoxylated$_8$ Bisphenol A dimethacrylate, triethylene glycol dimethacrylate, ethylene glycol dimethacrylate, tetraethylene glycol dimethacrylate, 1,4-butanediol dimethacrylate, 1,6-hexanediol dimethacrylate, neopentyl glycol dimethacrylate, 1,3-butylene glycol dimethacrylate, ethoxylated$_2$ Bisphenol A dimethacrylate, ethoxylated$_{10}$ Bisphenol A dimethacrylate, ethoxylated$_6$ Bisphenol A dimethacrylate, aliphatic urethane acrylates, aliphatic urethane oligomers, acrylic oligomers, polyether acrylate oligomers, polybutadiene dimethacrylate oligomers, diacrylate oligomers, triacrylate oligomers, polyester acrylate oligomers, epoxy acrylates, and aromatic urethane acrylates.

Suitable organic solvents include aliphatic hydrocarbons (such as petroleum ether, pentane, hexane, heptane and isododecane); cycloaliphatic hydrocarbons (such as cyclohexane, methylcyclohexane, ethylcyclohexane, tetrahydronaphthalene and decahydronaphthalene); terpenes and terpenoids (such as wood turpentine oil, pine oil, $\alpha$-pinene, $\beta$-pinene, dipentene and d-limonene); aromatic hydrocarbons (such as benzene, toluene, xylene, ethylbenzene, cumene, mestylene, pseudocumene, hemellitene, cymol and styrene); chlorinated hydrocarbons (such as dichloromethane, trichloromethane, ethyl chloride 1,2-dichloroethane, 1,1,1-trichloroethane, trichloroethylene, perchloroethylene and 1,2-dichloropropane); alcohols (such as methanol, ethanol, propanol, isopropyl alcohol, butanol, sec-butanol, tert-butanol, amyl alcohol, isoamyl alcohol, hexanol, heptanol, octanol, nonanol, methyisobutylcarbinol, 2-ethylbutanol, isoctyl alcohol, 2-ethylhexanol, isononanol, isodecanol, diisobutylcarbinol, cyclohexanol, methylcyclohexanol, trimethylcyclohexanol, benzyl alcohol, methylbenzyl alcohol, furfuryl alcohol, tetrahydrofurfuryl alcohol, and diacetone alcohol); ketones (such as acetone, methyl ethyl ketone, methyl propyl ketone, methyl isopropyl ketone, methyl butyl ketone, methyl isobutyl ketone, methyl amyl ketone, methyl isoamyl ketone, diethyl ketone, ethyl butyl ketone, ethyl amyl ketone, diisopropyl ketone, diisobutyl ketone, cyclohexanone, methylcyclohexanone, dimethylcyclohexanone, trimethylcyclohexanone, mesityl oxide, isophorone, and acetyl acetone); esters (such as methyl formate, ethyl formate, butyl formate, isobutyl formate, methyl acetate, propyl acetate, isopropyl acetate, butyl acetate, isobutyl acetate sec-butyl acetate, amyl acetate, isoamyl acetate, hexyl acetate, heptyl acetate, 2-ethylhexyl acetate, cyclohexyl acetate, benzyl acetate, propylene glycol diacetate, methyl propionate, ethyl propionate, propyl propionate, butyl propionate, pentyl propionate, ethyl butyrate, propyl butyrate, butyl butyrate, isobutyl butyrate, amyl butyrate, methyl isobutyrate, ethyl isobutyrate, isopropyl isobutyrate, isobutyl isobutyrate, methyl lactate, ethyl lactate, isopropyl lactate, butyl lactate, butyl glycolate, methyl glycol acetate, ethyl glycol acetate, butyl glycol acetate, ethyl diglycol acetate, butyl diglycol acetate, methoxypropyl acetate, ethoxypropyl acetate, 3-methoxybutyl acetate, ethyl 3-ethoxypropionate, dibasic ester, ethylene carbonate, propylene carbonate and butyrolactone); glycol ethers (such as methyl glycol, ethyl glycol, propyl glycol, isopropyl glycol, butyl glycol, hexyl glycol, phenyl glycol, methyl diglycol, ethyl diglycol, butyl diglycol, hexyl diglycol, methyl triglycol, ethyl triglycol, butyl triglycol, butyl tetraglycol, 1-methoxy-2-propanol, ethoxypropanol, isopropoxypropanol, butoxypropanol, isobutoxypropanol, tert-butoxypropanol, phenoxypropanol, methyl dipropylene glycol, isopropyl dipropylene glycol, butyl dipropylene glycol, methyl tripropylene glycol, butyl tripropylene glycol, diglycol dimethyl ether and dipropylene glycol dimethyl ether); ethers (such as diethyl ether, diisopropyl ether, dibutyl ether, methyl tert-butyl ether, tetrahydrofuran, dioxane, 2,2-dimethyl-4-hydroxymethyl-1,3-dioxane and 1,2-propylene oxide); and other solvents (such as dimethyl acetal, dimethylformamide, dimethylacetamide, dimethylsulfoxide, tetramethylene sulfone, carbon disulfide, furfurol, nitroethane, 1-nitropropane, 2-nitropropane, N-methylpyrrolidone, N-ethylpyrrolidone, N-cyclohexylpyrrolidone, N-(2-hydroxyethyl)pyrrolidone, 1,3-dimethyl-2-imidazolidinone and hexamethylenephosphoric triamide). These organic solvents may also be used to swell a matrix of the water soluble or hydrophilic acrylic polymer.

In another embodiment, the polymer matrix may be selected such that the matrix diffracts a different wavelength in response to a particular activator, such as metal ions in solution, organic molecules such as glucose, gasses in solution, antigens from various sources, antibodies from various sources, and viruses such as HIV. For example, a polymer matrix that has an acid functional group is reactive to an activator composition containing a base or vice-versa where the matrix has base functionality and the activator has acid functionality. The polymer matrix may be selected such that the matrix swells, shrinks or otherwise changes dimension and/or refractive index in response to various activators. The matrix may include an antigen, to which an antibody binds when exposed thereto. Similarly, the sensor may be based on enzyme and substrate pairs, chelating agents, complexing agents or aptamers. For certain sensors, the binding of an activator with the matrix may be sufficiently strong so that the activator remains attracted to, bound and/or within the matrix with little or no return of the sensor to its original state. In such embodiments, a covalent or ionic bond may occur between the activator and the matrix. One skilled in the art will appreciate that the various embodiments disclosed herein, as well as other embodiments within the scope of the invention, will have numerous applications in the environmental, medical pharmaceutical, metallurgy and chemical fields.

It will be appreciated that by selecting a particular matrix composition and an appropriate activator, the wavelength of diffraction of the matrix can be tuned. The radiation diffraction sensor of the present invention can be used for a variety of applications, including marking or identifying articles (such as on pharmaceutical packaging to authenticate the source of the pharmaceutical), security devices for authenticating a document or the like, as a sensor for the presence of a chemical species or as a novelty article, such as a toy. The radiation diffraction sensor of the present invention may be provided alone or in a form of a kit, along with an activator for contacting the sensor, which alters the diffracted radiation to a shifted wavelength.

The sensor of the present invention may be used to authenticate an article, such as to authenticate a document or device or to identify the source of a manufactured product. A document, such as a security card, that bears the sensor of the present invention would be considered to be authentic if the sensor responds to an activator. A "security card" includes documents or devices that authenticate the identity of the bearer thereof or permit access to a facility, such as in the form of a badge. The security card may identify the bearer of the card (e.g., a photo-identification card or a passport) or may function as a document or device that indicates that the bearer thereof is to be permitted access to a secure facility. For example, a security card may appear to be authentic, and upon application of an appropriate activator, the sensor on the card will exhibit a shift in the wavelength of diffracted radiation. A counterfeit security card would fail to exhibit that wavelength shift. Likewise, consumers of an item (such as a pharmaceutical product) provided in packaging bearing a sensor of the present invention can test the packaging for its authenticity by applying the appropriate activator thereto. Packaging which does not respond to the activator would be considered to be counterfeit, while packaging that responds to the activator would be considered to be authentic. Other consumer goods may include the sensor of the present invention, such as on the housing of a manufactured product (e.g. electronic devices) or on the surface of an article of clothing (e.g. shoes). The authenticity of the consumer goods may be tested by applying an activator thereto or activation of the sensor may be a novelty feature of the article. "Article" includes any product, including but not limited to those discussed herein, to which the present sensors can be applied.

An ordered periodic array of particles is formed on a substrate and is coated with a matrix that is cured as described above to produce a sensor. The substrate on which the sensor is formed may be a film or sheet which is subsequently applied to an article or another surface (such as the surface of a microporous sheet or of a metal foil). Alternatively, a surface of the article may serve as the substrate for producing the sensor. In that case, the ordered periodic array is formed on the article surface and the matrix composition is coated thereon. The sensor may be applied to a portion of the article via a mask to position the sensor at a particular location. Any remaining portion of the article surface may be coated or substantially coated with a suitable coating composition to produce a substrate in which the sensor is exposed, but any of the remaining substrate is coated. For example, a sensor according to the present invention can be applied to a microporous sheet, and the remainder of the sheet can be coated, laminated or the like. A security card can be prepared in this manner. In addition, the sensor is capable of being contacted by the appropriate activator, while the remainder of the card is protected from wear and tear and the like by a coating or lamination.

The sensor positioned on the article is contacted with an activator that shifts the wavelength of diffracted radiation. The shifted wavelength may be in the visible or invisible spectrum. The sensor returns at least substantially to its original state upon removal of the activator. For example, a hydrophilic acrylic polymer matrix is swellable by exposure to water. If an identification card bearing the sensor is contacted by water, a shift in the diffraction wavelength will occur, thereby evidencing authenticity of the identification card. When the water evaporates, the diffraction wavelength returns to substantially its original state.

As used herein, unless otherwise expressly specified, all numbers such as those expressing values, ranges, amounts or percentages may be read as if prefaced by the word "about", even if the term does not expressly appear. Any numerical range recited herein is intended to include all sub-ranges subsumed therein. Plural encompasses singular and vice versa. For example, while reference is made herein, including the claims, to "an" ordered periodic array, "a" matrix, "an" activator, and the like, more than one can be used, and although reference is made to changing the dimensions of the matrix, only one dimension might be changed. Also, as used herein, the term "polymer" is meant to refer to prepolymers, oligomers and both homopolymers and copolymers; the prefix "poly" refers to two or more.

These exemplary uses of radiation diffractive sensors as watermarks are not meant to be limiting. In addition, the following examples are merely illustrative of the present invention and are not intended to be limiting.

EXAMPLES

Example 1

Curable Acrylic Matrix

An ultraviolet radiation curable organic composition was prepared via the following procedure. A 50/50 blend (0.15 g) of diphenyl(2,4,6-trimethylbenzoyl)phosphine oxide and 2-hydroxy-2-methyl-propiophenone from Aldrich Chemical Company, Inc., Milwaukee, Wis., was added with stirring to 5.0 g of ethoxylated$_{20}$ trimethylolpropane triacrylate from Sartomer Company, Inc., Exton, Pa.

Example 2

Curable Acrylic Matrix

An ultraviolet radiation curable organic composition was prepared via the following procedure. A 50/50 blend (0.15 g) of diphenyl(2,4,6-trimethylbenzoyl)phosphine oxide and 2-hydroxy-2-methyl-propiophenone blend from Aldrich Chemical Company, Inc., Milwaukee, Wis., was added with stirring to 4.0 g of ethoxylated$_{20}$ trimethylolpropane triacrylate from Sartomer Company, Inc., Exton, Pa. Acrylic acid (1.0 g) from Aldrich Chemical Company, Inc. was then added to the mixture with stirring.

Example 3

Curable Acrylic Matrix

An ultraviolet radiation curable organic composition was prepared via the following procedure. A 50/50 blend (0.15 g) of diphenyl(2,4,6-trimethylbenzoyl)phosphine oxide and 2-hydroxy-2-methyl-propiophenone blend from Aldrich Chemical Company, Inc., Milwaukee, Wis., was added with stirring to 5 g of propoxylated$_2$ neopentyl glycol diacrylate from Sartomer Company, Inc., Exton, Pa.

Example 4

Array of Core-Shell Particles

A dispersion of polystyrene-divinylbenzene core/styrene-methyl methacrylate-ethylene glycol dimethacrylate-divinylbenzene shell particles in water was prepared via the following procedure.

Sodium bicarbonate (4.9 g) from Aldrich Chemical Company, Inc., was mixed with 4090 g deionized water and added to a 12-liter reaction kettle equipped with a thermocouple, heating mantle, stirrer, reflux condenser and nitrogen inlet. The mixture was sparged with nitrogen for 43 minutes with stirring and then blanketed with nitrogen. Aerosol MA80-I (46.8 g in 410 g deionized water) from Cytec Industries, Inc., was added to the mixture with stirring followed by a 48 g deionized water rinse. The mixture was heated to approximately 50° C. using a heating mantle. Styrene monomer (832.8 g), available from Aldrich Chemical Company, Inc., was added with stirring. The mixture was heated to 60° C. Sodium persulfate from the Aldrich Chemical Company, Inc. (12.5 g in 144 g deionized water) was added to the mixture with stirring. The temperature of the mixture was held constant for 40 minutes. Under agitation, divinylbenzene from Aldrich Chemical Company, Inc., (205.4 g) was added to the mixture and the temperature was held at approximately 60° C. for 2.3 hours. Brij 35 (polyoxyethylene(23) lauryl ether) from the Aldrich Chemical Company, Inc. (5.0 g in 100 g deionized water) was added to the mixture with stirring. Next, sodium persulfate from the Aldrich Chemical Company, Inc. (9.1 g in 900 g deionized water) was added to the mixture with stirring. A mixture of styrene (200 g), methyl methacrylate (478.8 g), ethylene glycol dimethacrylate (48 g) and divinylbenzene (30.2 g), all available from Aldrich Chemical Company, Inc., was added to the reaction mixture with stirring. Sipomer COPS-I (3-Allyloxy-2-hydroxy-1-propanesulfonic acid 82.7 g) from Rhodia, Inc. Cranbury, NJ., was added to the reaction mixture with stirring and was followed by a (100 g) deionized water charge. The temperature of the mixture was maintained at 60° C. for approximately 4.0 hours.

The resulting polymer dispersion was filtered through a five-micron filter bag. The polymer dispersion was ultrafiltered using a 4-inch ultrafiltration housing with a 2.41-inch polyvinylidine fluoride membrane, both from PTI Advanced Filtration, Inc., Oxnard, Calif., and pumped using a peristaltic pump at a flow rate of approximately 170 ml per second. Deionized water (2985 g) was added to the dispersion after 3000 g of ultrafiltrate had been removed. This exchange was repeated several times until 11349 g of ultrafiltrate had been replaced with 11348 g deionized water. Additional ultrafiltrate was then removed until the solids content of the mixture was 44.8 percent by weight.

The material was applied via slot-die coater from Frontier Industrial Technology, Inc., Towanda, Pa. to a 2 mil thick polyethylene terephthalate (PET) substrate and dried at 180° F for 40 seconds to a dry thickness of approximately 7 microns. The resulting material diffracted light at 518 nm measured with a Cary 500 spectrophotometer from Varian, Inc.

Example 5

Water Soluble Fixed Array

Material prepared in Example 1 was applied to the fixed array of polystyrene-divinylbenzene core/styrene-methyl methacrylate-Ethylene glycol dimethacrylate-divinylbenzene shell particles from Example 4 using a drawdown bar. A piece of 2 mil thick PET film was then placed upon the deposited material from Example 1 so that the material was entirely covered. A roller was used on the top side of the PET substrate to spread out and force the UV curable coating from Example 1 into the interstitial spaces of the fixed array from Example 4. The sample was ultraviolet radiation cured using a 100 W mercury lamp. The two layers of PET were then separated.

The film exhibited a green color when viewed perpendicular or 0 degrees to the observer and a blue color when viewed at 45 degrees or greater to the observer. The diffraction wavelength of the film was measured using a Cary 500 spectrophotometer. Subsequently, the film was exposed to water and the diffraction wavelength was measured again. The film was measured one final time after the water evaporated. The results listed below in Table 1 show that the diffraction wavelength of the material increased with application of water and returned to essentially its original state upon removal of the water.

TABLE 1

| Sample | Diffraction Wavelength |
| --- | --- |
| Initial State | 560 nm |
| Hydrated (H$_2$O) | 602 nm |
| Dried | 558 nm |

Example 6

Functional Group Swellable Fixed Array

The procedure of Example 5 was repeated except the material from Example 2 (containing acid groups) was used in place of material from Example 1. The film exhibited a green color when viewed perpendicular or 0 degrees to the observer and a blue color when viewed at 45 degrees or greater to the observer. The diffraction wavelength of the film was measured using a Cary 500 spectrophotometer. Subsequently, the film was exposed to water and the diffraction wavelength was measured again. The film was exposed to a 5% solution of a base (dimethylethanolamine (DMEA)) in deionized water, and the diffraction wavelength was remeasured. The film was measured one final time after the DMEA solution evaporated. The results listed in Table 2 show that the acrylic polymer matrix material of the film containing acid groups was swellable by both water and a base and returned to essentially its original state upon removal of the water and base.

The product of Example 6 differed from the product of Example 5 by the inclusion of acid functionality in the matrix material of Example 6. Both products swelled when contacted with water as demonstrated by the change in the wavelength of diffracted radiation from 560 nm to 602 nm. The product of Example 6 was further altered when contacted with a base (DMEA) as demonstrated by the further increase in the wavelength of diffracted radiation to 623 nm.

TABLE 2

| Sample | Diffraction Wavelength |
| --- | --- |
| Initial State | 560 nm |
| Hydrated (H$_2$O) | 602 nm |
| Hydrated (H$_2$O and DMEA) | 623 nm |
| Dried (H$_2$O and DMEA) | 562 nm |

Example 7

Organic Solvent Swellable Fixed Array

The procedure of Example 5 was repeated except material from Example 3 was used in place of material from Example 1. The film exhibited a green color when viewed perpendicular or 0 degrees to the observer and a blue color when viewed at 45 degrees or greater to the observer. The diffraction wavelength of the film was measured using a Cary 500 spectrophotometer. Subsequently, the film was exposed to water and the diffraction wavelength was measured again with essentially no change. The film was then exposed to 95% denatured ethanol and the diffraction wavelength was measured. The film was measured one final time after the ethanol had evaporated. The results listed in Table 3 show that the film was not swellable by water, yet was swellable by ethanol and returned to nearly its original state upon removal of the ethanol.

TABLE 3

| Sample | Diffraction Wavelength |
| --- | --- |
| Initial State | 556 nm |
| Hydrated (H$_2$O) | 556 nm |
| Ethanol Exposed | 610 nm |
| Ethanol Evaporated | 564 nm |

As demonstrated herein, the radiation diffraction material of the present invention may be used to sense the presence of water or organic solvent.

While the preferred embodiments of the present invention are described above, obvious modifications and alterations of the present invention may be made without departing from the spirit and scope of the present invention. The scope of the present invention is defined in the appended claims and equivalents thereto.

The invention claimed is:

1. A radiation diffraction sensor comprising:
   an ordered periodic array of particles formed on a substrate; and
   a solid matrix composition coated onto the array of particles;
   wherein the matrix composition is selected to be responsive to an activator, such that exposure to the activator shifts the wavelength of radiation diffracted by the sensor from a first wavelength to a second wavelength.

2. The sensor of claim 1 wherein the wavelength of diffracted radiation substantially returns to the first wavelength when the activator is removed from the sensor.

3. The sensor of claim 1 wherein the matrix comprises a hydrophilic acrylic polymer that is responsive to water.

4. The sensor of claim 1 wherein the matrix comprises a polymer that is responsive to an organic solvent.

5. The sensor of claim 1 wherein said substrate is a film.

6. The sensor of claim 1 wherein said substrate is a microporous sheet.

7. The sensor of claim 1 wherein said substrate is a surface of an article.

8. The sensor of claim 7 wherein said surface is a packaging and/or a housing of an article.

9. A method of producing a sensor comprising:
   forming an ordered periodic array of particles on a substrate;
   coating the array of particles with a matrix; and
   curing the matrix to fix the array of particles within the matrix, wherein the matrix is selected to be responsive to an activator, such that exposure to the activator shifts the wavelength of radiation diffracted by the sensor to a shifted wavelength.

10. The method of claim 9 wherein the activator comprises water.

11. The method of claim 10 wherein the matrix comprises a hydrophilic acrylic polymer.

12. The method of claim 9 wherein the activator comprises an organic solvent.

13. The method of claim 12 wherein the matrix comprises a polymer responsive to an organic solvent.

14. The method of claim 9 wherein the shifted wavelength is in the visible spectrum.

15. The method of claim 9 wherein the shifted wavelength is outside the visible spectrum.

16. The method of claim 9 further comprising removing the sensor from the substrate.

17. The method of claim 16 further comprising comminuting the sensor into particulate form.

18. The method of claim 9 wherein the activator comprises a functional group reactive with the matrix.

19. An article having a sensor produced according to the method of claim 9.

20. A method of authenticating an article comprising:
    forming an ordered periodic array of particles on a substrate;
    coating the array of particles with a matrix;
    curing the matrix to fix the array of particles within the matrix to produce a sensor that diffracts radiation at a first wavelength;
    applying the sensor to an article; and
    contacting the sensor with an activator such that the activator shifts the wavelength of diffraction, wherein the shifted wavelength of diffraction indicates the authenticity of the article.

21. The method of claim 20 wherein the shifted wavelength is in the visible spectrum.

22. The method of claim 20 wherein the shifted wavelength is outside the visible spectrum.

23. The method of claim 20 wherein the substrate is a film that is applied to the article.

24. The method of claim 20 wherein the substrate is a surface of the article.

25. The method of claim 20 wherein the substrate is a microporous sheet.

26. The method of claim 20 further comprising removing the activator from the sensor so that the wavelength of diffracted radiation substantially returns to the first wavelength.

27. The method of claim 20 wherein the article is a security card.

28. The method of claim 20 wherein the substrate is flexible.

29. The method of claim 20 wherein the substrate is EVA foam.

30. The method of claim 20 wherein the substrate is metal.

* * * * *